(12) United States Patent
Toyoda

(10) Patent No.: US 6,628,501 B2
(45) Date of Patent: Sep. 30, 2003

(54) CAPACITIVE MOISTURE SENSOR

(75) Inventor: Inao Toyoda, Anjo (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/151,009

(22) Filed: May 21, 2002

(65) Prior Publication Data

US 2003/0002238 A1 Jan. 2, 2003

(30) Foreign Application Priority Data

Jun. 15, 2001 (JP) ........................................ 2001-182032

(51) Int. Cl.$^7$ ................................................. H01G 4/06
(52) U.S. Cl. ...................... 361/303; 361/286; 361/287; 361/311; 361/313
(58) Field of Search ................................ 361/303, 302, 361/286, 287, 311, 313; 357/25, 23.15, 23.14, 53, 57

(56) References Cited

U.S. PATENT DOCUMENTS

| | | | |
|---|---|---|---|
| 4,305,112 A | | 12/1981 | Heywang et al. |
| 4,638,346 A | * | 1/1987 | Inami et al. |
| 4,651,121 A | * | 3/1987 | Furubayashi et al. |
| 4,737,852 A | * | 4/1988 | Dohkoshi et al. |
| 4,831,493 A | * | 5/1989 | Wllson et al. |
| 4,849,798 A | * | 7/1989 | Watanabe |
| 6,445,565 B1 | * | 9/2002 | Toyoda et al. |
| 6,456,482 B1 | * | 9/2002 | Shih et al. |

FOREIGN PATENT DOCUMENTS

| | | |
|---|---|---|
| GB | 2149922 | 6/1985 |
| JP | A-62-88951 | 4/1987 |
| JP | A-5-142182 | 6/1993 |
| JP | A-6-58900 | 3/1994 |
| JP | B2-6-105235 | 12/1994 |
| JP | A-7-20080 | 1/1995 |
| JP | A-9-127259 | 5/1997 |

* cited by examiner

Primary Examiner—Dean A. Reichard
Assistant Examiner—Nguyen Ha
(74) Attorney, Agent, or Firm—Posz & Bethards, PLC

(57) ABSTRACT

A capacitive moisture sensor includes a semiconductor substrate, which has a hole. A silicon oxide film is located to close the hole. A pair of electrodes is located on the silicon oxide film. Each electrode is in the shape of a comb, and the electrodes mesh with each other. A silicon nitride film is located on the electrodes to cover and protect the electrodes and on the silicon oxide film between the electrodes. A moisture-sensitive film, the dielectric constant of which varies in response to ambient moisture, is located on the silicon nitride film. The thickness of the substrate is substantially zero under the electrodes to eliminate the parasitic capacitance between each electrode and the substrate.

10 Claims, 4 Drawing Sheets

CAPACITIVE MOISTURE SENSOR

CROSS REFERENCE TO RELATED APPLICATION

This application is based on and incorporates herein by reference Japanese Patent Application No. 2001-182032 filed on Jun. 15, 2001.

BACKGROUND OF THE INVENTION

1. Field of the Invention

The present invention relates to a capacitive moisture sensor. The sensor includes a pair of electrodes and a moisture-sensitive film, which is located between the electrodes. The dielectric constant of the film varies in response to ambient moisture. The ambient moisture is sensed on a basis of the capacitance change between the electrodes.

2. Description of the Related Art

A capacitive moisture sensor is utilized to measure indoor moisture for an air conditioner, outdoor moisture for meteorological observation, and so on. This type of capacitive moisture sensors are proposed in JP-B2-6-105235, JP-A-55-66749, and JP-A-60-166854. However, in the sensors of the publications, a bottom electrode, a moisture-sensitive film, and a thin top electrode, which is moisture permeable, are located in this order on a substrate, and the top electrode is exposed to the atmosphere. Therefore, the sensor is relatively poorly moisture-proof and has relatively poor durability. As a solution to the poor durability issue, a different type of capacitive moisture sensor is proposed. In the different type of sensor, an insulating film is located on a substrate, a pair of electrodes is located on the insulating film, and a moisture-sensitive film is located on the electrodes to cover the electrodes.

However, the different type of sensor has parasitic capacitance between each electrode and the substrate. In general, the capacitance change amount corresponding to ambient moisture change amount is relatively small in a capacitive moisture sensor, so the parasitic capacitance worsens the precision and accuracy in measurement of the ambient moisture.

SUMMARY OF THE INVENTION

The present invention has been made in view of the above aspects with an object to provide a capacitive moisture sensor that has a desired precision and accuracy in measurement of ambient moisture without exposing either electrode of a capacitor for the measurement to the atmosphere.

In the present invention, a capacitive moisture sensor includes a semiconductor substrate, which has a hole. A silicon oxide film is located to close the hole. A pair of electrodes is located on the silicon oxide film. Each electrode is in the shape of a comb, and the electrodes mesh with each other. A silicon nitride film is located on the electrodes to cover and protect the electrodes and on the silicon oxide film between the electrodes. A moisture-sensitive film, the dielectric constant of which varies in response to ambient moisture, is located on the silicon nitride film. The thickness of the substrate is substantially zero under the electrodes to eliminate the parasitic capacitance between each electrode and the substrate.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

The present invention will be described in detail with reference to an embodiment.

Figure 1:
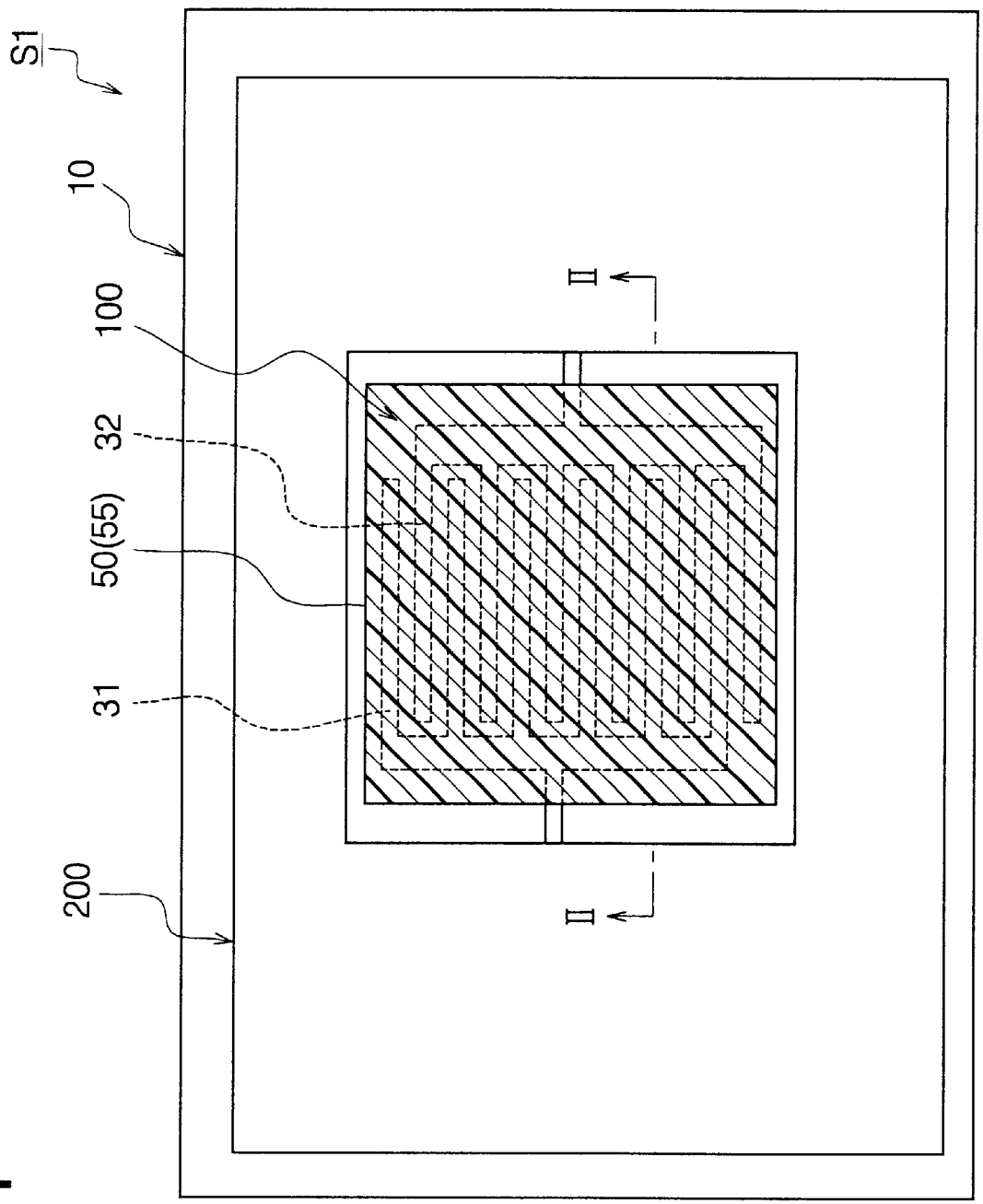
FIG. 1 is a plan view of a capacitive moisture sensor according to the present invention.
Figure 2:
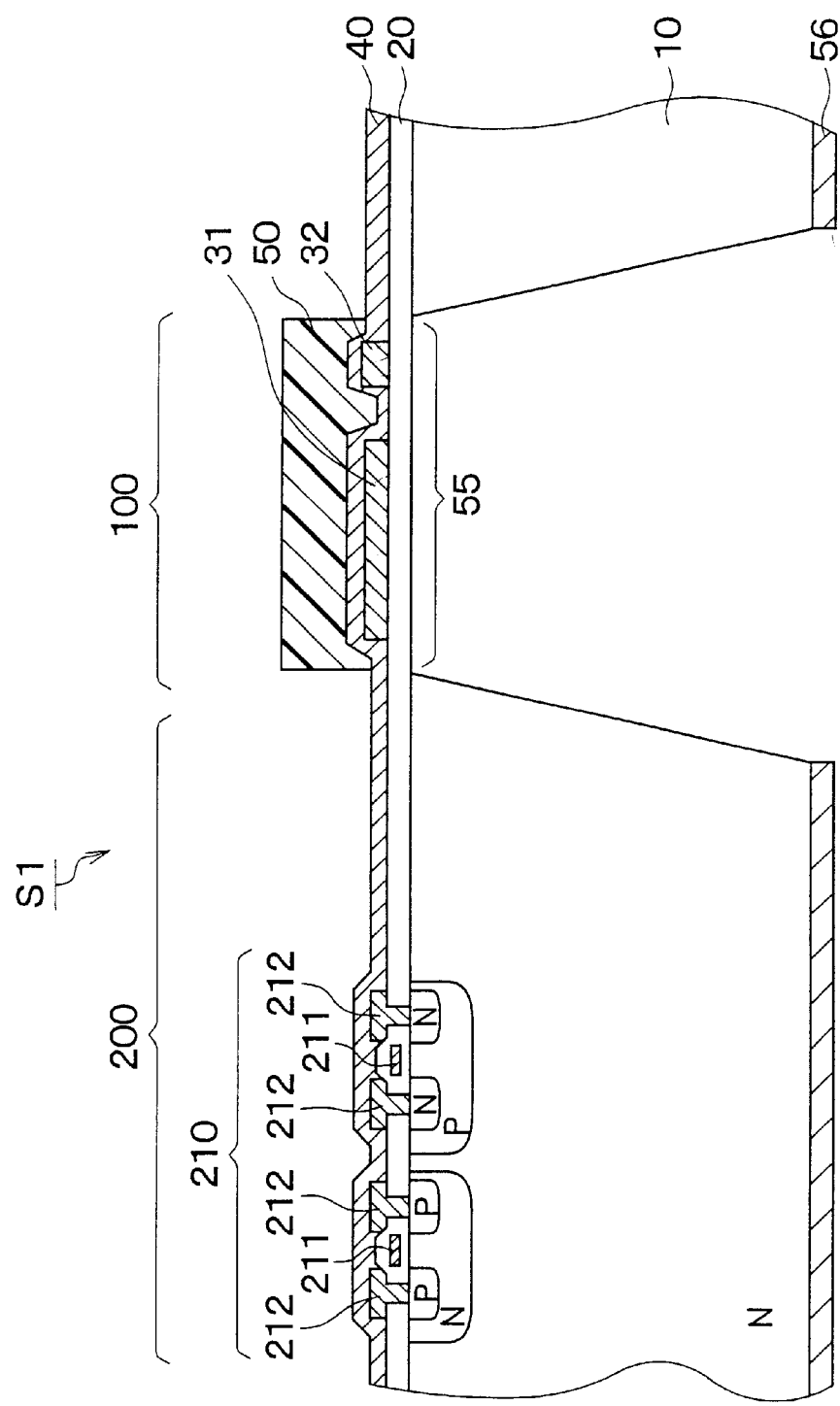
FIG. 2 is a cross-sectional view of the capacitive moisture sensor taken along the line II—II in FIG. 1.

As shown in FIGS. 1 and 2, a capacitive moisture sensor S1 includes a semiconductor substrate 10. The substrate 10 is made of an n-type single crystal silicon and has a front surface and a back surface. The front surface and the back surface look in the opposite directions. The substrate 10 has a hole. A silicon oxide film 20, which is a first insulating film, is located on the front surface and closes the hole in the substrate 10, as shown in FIG. 2. A silicon nitride film 56 is located on the back surface. The hole is formed by etching the substrate 10 from the back surface using the silicon nitride film 56 as an etching mask. A pair of electrodes 31,32 is located on the silicon oxide film 20 located above the hole. As shown FIG. 1, each electrode 31, 32 is in the shape of a comb, and the electrodes 31, 32 mesh with each other with a predetermined distance to increase the facing area between the electrodes 31, 32. Therefore, a desired capacitance between the electrodes 31, 32 is provided with relatively small sizes of the electrodes 31, 32.

Each electrode 31, 32 in FIG. 1 is made of aluminum (Al). Other materials such as aluminum-silicon (Al—Si), which includes aluminum and a small amount of silicon, e.g., 0.1 to 0.3%, titan (Ti), gold (Au), copper (Cu), and polycrystalline silicon (Poly-Si) may be used. The materials are commonly used in semiconductor manufacturing processes.

Each electrode 31, 32 is covered with a silicon nitride film 40, which is a second insulating film, as shown in FIG. 2. The second insulating film is not limited to the silicon nitride film 40. However, the silicon nitride film 40 is preferred to decrease the capacitance loss between the electrodes 31, 32 and increase the sensitivity of ambient moisture measurement because the silicon nitride film 40 has a relatively high dielectric constant. In the sensor S1, as shown in FIG. 2, a surface of the silicon oxide film 20 between the electrodes 31, 32 is also covered with the silicon nitride film 40. However, the surface between the electrodes 31, 32 does not need to be covered. A moisture-sensitive film 50, the dielectric constant of which varies in response to ambient moisture, is located on the silicon nitride film 40 on the electrodes 31, 32 and located on the silicon nitride film 40 between the electrodes 31, 32. A moisture-sensing area 100 is defined by the circumference of the moisture-sensitive film 50, as shown in FIG. 1. At the moisture-sensing area 100, the capacitance between the electrodes 31, 32 varies in response to ambient moisture variation, so the ambient moisture is sensed on a basis of the capacitance change between the electrodes 31, 32.

In the sensor S1 in FIG. 1, the moisture-sensitive film 50 is made of polyimide resin. Other hygroscopic organic polymers such as cellulose acetate butyrate may be used for the moisture-sensitive film 50. The polyimide resin for the moisture-sensitive film 50 has a hardening temperature of about 350° C. The other hygroscopic organic polymers need to have a hardening temperature lower than 400° C. because semiconductor elements, which are formed on a periphery of the substrate 10, are not damaged as long as the temperature is lower than 400° C. Because water molecules are polar ones, the dielectric constant of the moisture-sensitive film 50 changes significantly in response to the water content of the moisture-sensitive film 50 and so does the capacitance between the electrodes 31, 32. Thus, the ambient moisture is sensed on a basis of the capacitance change between the electrodes 31, 32.

In the sensor S1, as shown in FIG. 2, the electrodes 31, 32 are supported only by the silicon oxide film 20. That is, the thickness of the substrate 10 is substantially zero under the electrodes 31, 32 as viewed in FIG. 2. Therefore, the parasitic capacitance between each electrode 31, 32 and the substrate 10 is eliminated. Thus, the precision and accuracy in the measurement of ambient moisture is not worsened by the parasitic capacitance.

As shown in FIG. 2, a membrane 55 includes the silicon oxide film 20, the electrodes 31, 32, the silicon nitride film 40, and the moisture-sensitive film 50. In the sensor S1, the moisture-sensitive film 50 has the same size as the membrane 55.

As shown in FIG. 1, a peripheral device area 200, where an electric signal corresponding to the capacitance change between the electrodes 31, 32 is processed, is located around the moisture-sensing area 100. As shown in FIG. 2, the peripheral device area 200 includes a plurality of complementary metal oxide semiconductor (C-MOS) transistors 210. The transistors 210 include a plurality of gate electrodes 211, which are made of polycrystalline silicone, and a plurality of pairs of source and drain electrodes 212, which are made of aluminum. Other electronic devices such as a Bi-CMOS transistor may be included in the peripheral device area 200 of the sensor S1.

In the sensor S1, the peripheral device area 200 and the electrodes 31, 32 are electrically connected by a plurality of wiring lines (not illustrated) to form a CR type oscillator circuit, so the capacitance change between the electrodes 31, 32 is transduced to frequency change to sense ambient moisture. The silicon nitride film 40 is located between each electrode 31, 32 and the moisture-sensitive film 50 to protect the electrodes 31, 32 from moisture, which permeates into the moisture-sensitive film 50 from ambient air. Therefore, the electrodes 31, 32 can be made of a relatively affordable material such as aluminum, which is used in semiconductor device manufacturing process, instead of relatively expensive noble metals, which are relatively moisture-proof. In addition, a leak current between the electrodes 31, 32 is prevented because the electrodes 31, 32 are insulated by the silicon nitride film 40.

As described later, the sensor S1 is manufactured using semiconductor manufacturing technology, so the sensor S1 is readily miniaturized and integrated at relatively low cost. In addition, the peripheral device area 200 and the electrodes 31, 32 are integrated on the semiconductor substrate 10, so the stray capacitance that exists between the peripheral device area 200 and each electrode 31, 32 is decreased. Thus, it is possible to reduce the area of the electrodes 31, 32 and provide a relatively compact moisture sensor.

Figure 3A:
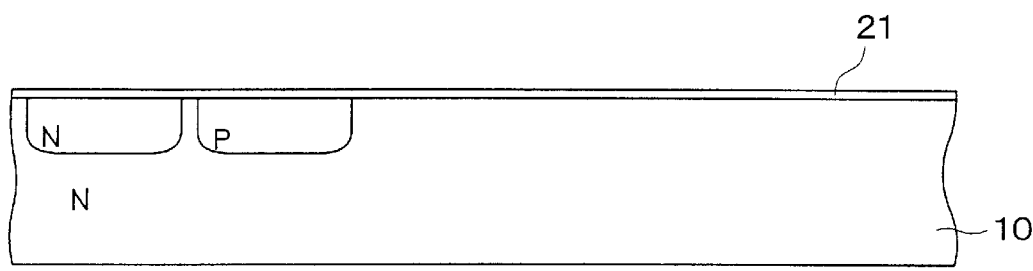
FIGS. 3A to 3C are cross-sectional views showing steps of a process for manufacturing the capacitive moisture sensor in FIG. 1.
Figure 3B:
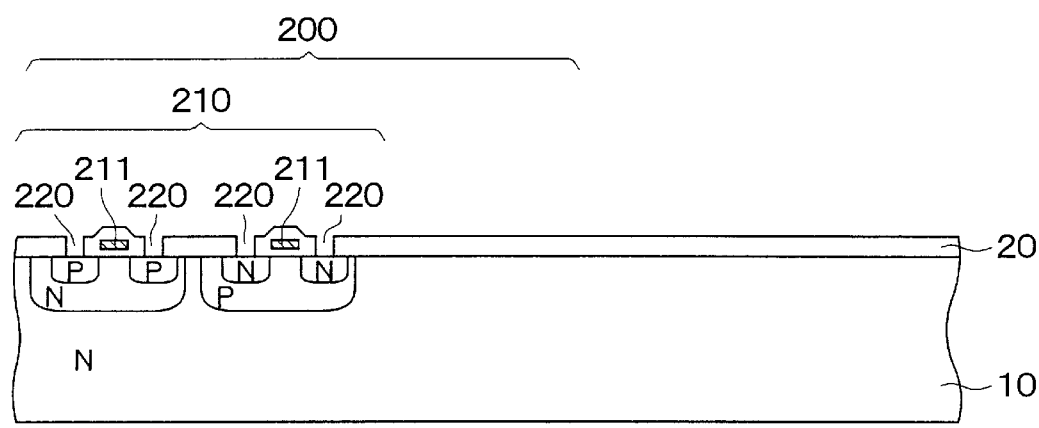

The sensor S1 is manufactured as follows using semiconductor manufacturing technology. As shown in FIG. 3A, impurity ions are implanted in a plurality of predetermined regions of the front surface of substrate 10, and the front surface is oxidized to form a thermal silicon oxide film 21. Then, a poly-Si layer is deposited by chemical vapor deposition (CVD), and the gate electrodes 211 are formed from the poly-Si layer by photolithography and etching. The silicon oxide film 20 and a plurality of pairs of source and drain regions are formed in a known manner using CVD, photolithography, ion implantation, thermal diffusion, and so on. When the silicon oxide film 20 is formed by CVD, the thermal silicon oxide film 21 is integrated with the silicon oxide film 20. Afterward, contact holes 220 are made in the silicon oxide film 20 using photolithography and etching to permit the source and drain regions in the peripheral device area 200 to communicate with the space outside of the silicon oxide film 20, as shown in FIG. 3B.

Subsequently, a conductive film such as aluminum is deposited by sputtering or vacuum evaporation. The electrodes 31, 32 and a metallized layer including the source and drain electrodes 212, the wiring lines, and a plurality of pads (not illustrated) is formed from the conductive film using photolithography and etching. The electrodes 31, 32 and the metallized layer may be formed respectively from a different type of conductive film. However, it is preferred that the same conductive film is used as in the sensor S1 because the number of steps such as film deposition, photolithography, or etching in the manufacturing process of the sensor S1 is reduced and so is manufacturing cost.

Figure 3C:
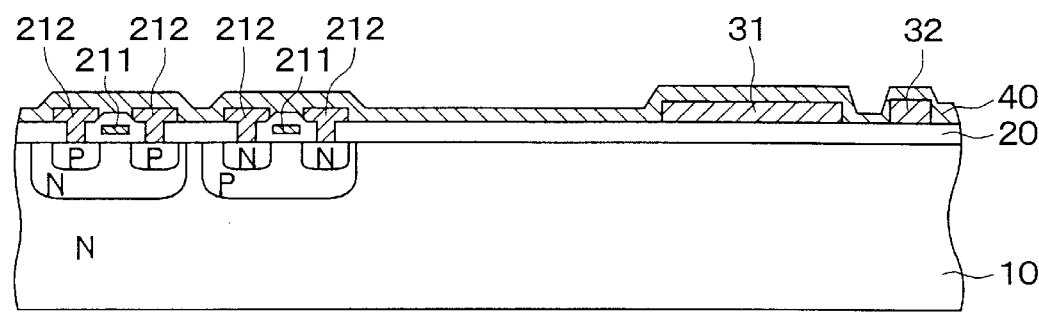

Then, the silicon nitride film 40 is deposited by plasma CVD to cover the metallized layer and the electrodes 31, 32, as shown in FIG. 3C. The silicon nitride film 40 on the pads, through which the peripheral device area 200 is electrically connected to a circuit outside of the capacitive moisture sensor S1, is removed using photolithography and etching.

Figure 4:
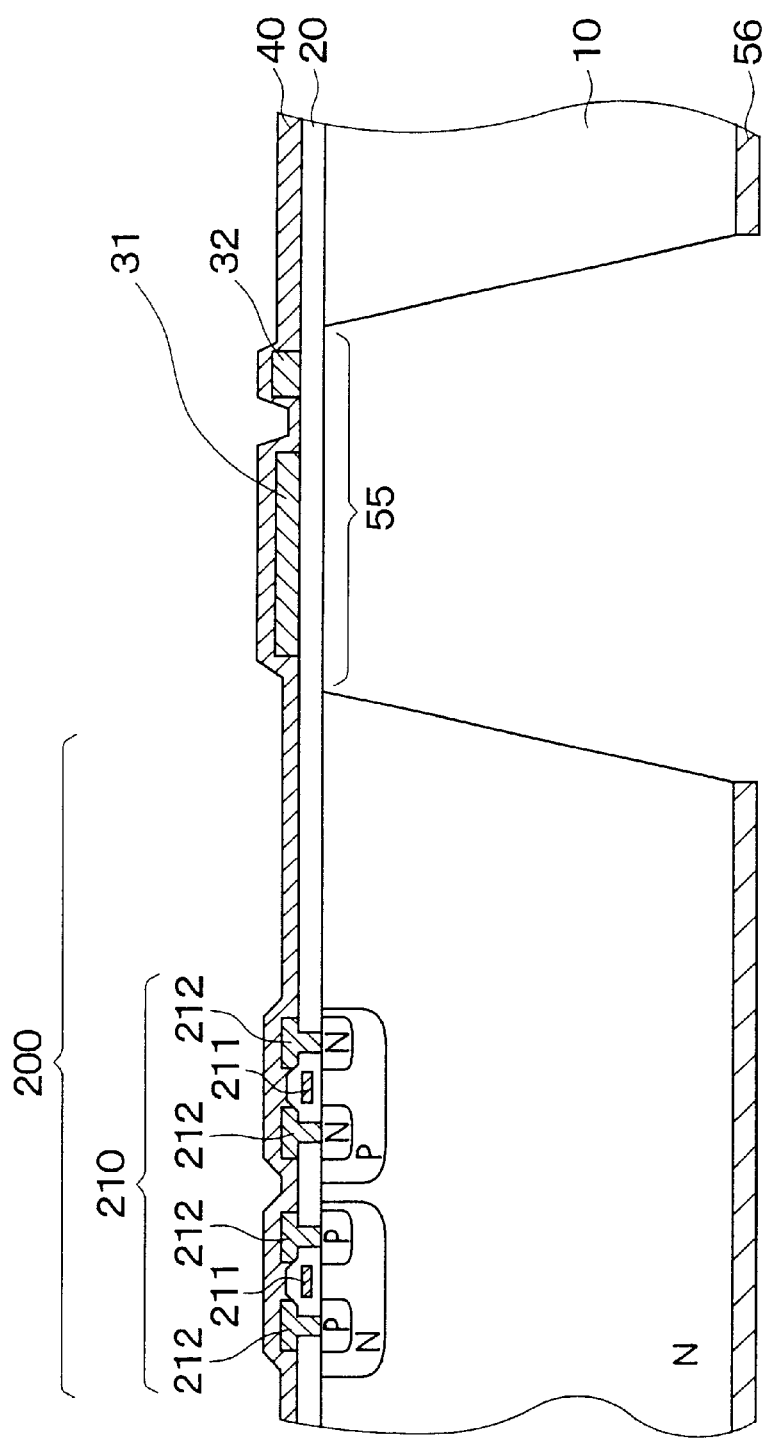
FIG. 4 is a cross-sectional view showing another step of the process following the step in FIG. 3C.

The silicon nitride film 56 is formed on the back surface. The silicon nitride film 56 is partially removed using photolithography and etching to form an opening beneath the moisture-sensing area 100 in the vertical direction of FIG. 4. Then, the membrane 55 is formed by etching anisotropically the substrate 10 from the back surface using the silicon nitride film 56 as an etching mask, as shown in FIG. 4. Etchants such as potassium hydroxide (KOH) aqueous solution or tetramethyl ammonium hydroxide (TMAH) aqueous solution may be used for the etching.

Finally, to complete the sensor S1 shown in FIGS. 1 and 2, the moisture-sensitive film 50 is formed on the silicon nitride film 40 by spin-coating polyimide resin, hardening the polyimide resin, and removing the polyimide resin except for a portion of the polyimide resin, which is located in the moisture-sensing area 100. The moisture-sensitive film 50 may also be formed by printing the polyimide resin only on the silicon nitride film 40 located in the moisture-sensing area 100 and by hardening the printed polyimide resin.

Modifications

In the sensor S1, the first insulating film may be a silicon nitride film. However, the dielectric constant of the silicon nitride film is higher than the silicon oxide film 20, so the silicon oxide film 20 is preferred to decrease the parasitic capacitance between each wiring line and the substrate 10.

The sensor S1 has the peripheral device area 200, where an electric signal corresponding to the capacitance change between the electrodes 31, 32 is processed, around the moisture-sensing area 100. However, the sensor S1 may have only the moisture-sensing area 100. In that case, an electric signal processing circuit, which is equivalent to the peripheral device area 200, is provided outside of the sensor S1 and is electrically connected to the moisture-sensing area 100 using leads or bonding wires.

In the sensor S1, the peripheral device area 200 and the electrodes 31, 32 are electrically connected to form the CR type oscillator circuit, and the capacitance change between the electrodes 31, 32 is transduced to frequency change to sense ambient moisture. However, instead of the CR type oscillator circuit, a switched capacitor circuit may be formed using the peripheral device area 200 and the electrodes 31, 32, and the capacitance change between the electrodes 31, 32 may be transduced to voltage change to sense ambient moisture.

What is claimed is:

1. A capacitive moisture sensor comprising:
    a semiconductor substrate;
    a first insulating film that is located on a surface of the substrate;
    a pair of electrodes that is located on the first insulating film;
    a second insulating film that is located on the electrodes to cover and protect the electrodes; and
    a moisture-sensitive film having a dielectric constant that varies in response to ambient moisture, wherein the moisture-sensitive film is located on the second insulating film on the electrodes and is also located on one of the first insulating film and the second insulating film between the electrodes,
    wherein the semiconductor substrate has a hole under the electrodes to decrease the parasitic capacitance between each electrode and the semiconductor substrate.

2. The capacitive moisture sensor as in claim 1, wherein the first insulating film is exposed at the bottom of the hole.

3. A capacitive moisture sensor comprising:
    a semiconductor substrate;
    a first insulating film that is located on a surface of the substrate;
    a pair of electrodes that is located on the first insulating film;
    a second insulating film that is located on the pair of electrodes to cover and protect the pair of electrodes; and
    a moisture-sensitive film having a dielectric constant that varies in response to ambient moisture, the moisture-sensitive film located on the second insulating film above the pair of electrodes and also located on one of the first insulating film and the second insulating film between the pair of electrodes,
    wherein the thickness of the semiconductor substrate is substantially zero under the pair of electrodes for decreasing parasitic capacitance between each of the pair of electrodes and the substrate.

4. The capacitive moisture sensor as in claim 3, wherein the each of the pair of electrodes is in the shape of a comb and wherein the pair of electrodes mesh with each other.

5. The capacitive moisture sensor as in claim 3, wherein the first insulating film is made of silicon oxide.

6. The capacitive moisture sensor as in claim 3, wherein the second insulating film is made of silicon nitride.

7. The capacitive moisture sensor as in claim 3, wherein the moisture-sensitive film includes polyimide resin.

8. A method for manufacturing a capacitive moisture sensor, the method comprising steps of:
    providing a semiconductor substrate that has a front surface and a back surface;
    forming a first insulating film on the front surface;
    forming a pair of electrodes on the first insulating film;
    forming a second insulating film on the electrodes;
    etching anisotropically the semiconductor substrate from the back surface to form a hole in the semiconductor substrate under the pair of electrodes; and
    forming a moisture-sensitive film, the dielectric constant of which varies in response to ambient moisture, on the second insulating film on the pair of electrodes and on one of the first insulating film and the second insulating film between the pair of electrodes.

9. The method as in claim 8 includes a step of forming a silicon nitride film on the back surface as an etching mask and another step of forming an opening in the silicon nitride film to etch the substrate through the opening.

10. The method in claim 8, wherein the etching anistropically of the semiconductor substrate further comprises etching until the first insulating film is exposed at the bottom of the hole.

* * * * *